United States Patent
Prado et al.

(10) Patent No.: US 7,759,938 B2
(45) Date of Patent: Jul. 20, 2010

(54) APPARATUS AND METHOD FOR VARYING MAGNETIC FIELD STRENGTH IN MAGNETIC RESONANCE MEASUREMENTS

(75) Inventors: Pablo J. Prado, San Diego, CA (US); Sankaran Kumar, San Marcos, CA (US); Erik Edmund Magnuson, Cardiff, CA (US)

(73) Assignee: Morpho Detection, Inc., Newark, CA (US)

(*) Notice: Subject to any disclaimer, the term of this patent is extended or adjusted under 35 U.S.C. 154(b) by 0 days.

(21) Appl. No.: 11/966,331

(22) Filed: Dec. 28, 2007

(65) Prior Publication Data
US 2009/0167304 A1 Jul. 2, 2009

Related U.S. Application Data

(60) Provisional application No. 60/888,185, filed on Feb. 5, 2007.

(51) Int. Cl.
*G01V 3/00* (2006.01)
(52) U.S. Cl. ......................... 324/319; 324/320; 335/296
(58) Field of Classification Search ............... 324/319, 324/320; 335/296
See application file for complete search history.

(56) References Cited

U.S. PATENT DOCUMENTS

| | | | | |
|---|---|---|---|---|
| 4,122,386 A * | 10/1978 | Tomita et al. | ............... | 324/320 |
| 4,636,756 A * | 1/1987 | Ito et al. | ...................... | 333/202 |
| 4,672,346 A * | 6/1987 | Miyamoto et al. | .......... | 335/296 |
| 4,673,882 A * | 6/1987 | Buford | ........................ | 324/320 |
| 4,870,380 A * | 9/1989 | McGinley | .................... | 335/296 |
| 5,347,252 A * | 9/1994 | Ries | ........................... | 335/299 |
| 5,357,958 A * | 10/1994 | Kaufman | .................... | 600/410 |
| 5,431,165 A * | 7/1995 | Sellers | ....................... | 600/422 |
| 6,346,816 B1 * | 2/2002 | Damadian et al. | ........... | 324/319 |
| 6,448,772 B1 | 9/2002 | Aoki | | |
| 7,148,689 B2 * | 12/2006 | Huang et al. | ................ | 324/319 |

OTHER PUBLICATIONS

Barlow, David B., Kraus, Jr., Robert H., Meyer, Ross E., "Variable-Field Permanent Magnet Dipole", Los Alamos National Laboratory, 13th International Conference on Magnet Technology, Victoria Conference Centre, Victoria, B.C, Canada, Sep. 20-24, 1993.

* cited by examiner

*Primary Examiner*—Louis M Arana
(74) *Attorney, Agent, or Firm*—Armstrong Teasdale LLP

(57) ABSTRACT

Apparatus and method for varying field strength in a magnetic resonance system while keeping a relatively uniform magnetic field distribution. In an embodiment, a two-pole, generally u-shaped magnet assembly generates a static and uniform magnetic field. The magnet assembly includes two facing magnet poles separated by an air gap. Holes may be formed with the magnet poles. The field control rods may be placed at a pre-determined distance into these holes and symmetrically or asymmetrically moved across each magnet poles in a controlled manner to change the magnetic field strength while keeping the uniform magnetic field distribution. Maximum magnetic field strength may occur when the rods are removed. Minimum magnetic field strength may occur when the rods are fully inserted.

20 Claims, 2 Drawing Sheets

APPARATUS AND METHOD FOR VARYING MAGNETIC FIELD STRENGTH IN MAGNETIC RESONANCE MEASUREMENTS

CROSS REFERENCE TO RELATED APPLICATIONS

This application claims priority to U.S. Provisional Patent Application Ser. No. 60/888,185, entitled "Apparatus and Methods for Varying Magnetic Field Strength in Magnetic Resonance Measurements," filed on Feb. 5, 2007, which is hereby incorporated by reference herein in its entirety

BACKGROUND

1. Field of the Invention

The present disclosure relates to magnetic resonance systems generally, and more particularly, to an apparatus and methods for varying field strength in a magnetic resonance system while keeping a relatively uniform magnetic field distribution.

2. Discussion of Related Art

A need exists, particularly in developing countries, to reliably, inexpensively, and non-invasively measure iron stores within humans to help in the clinical management and treatment of a number of diseases, including hematological malignancies, liver disease, hemoglobinopathies, hereditary hemochromatosis, thalassemia, and sickle cell disease, that can be complicated and exacerbated by iron overload. For example, in combination with hereditary hemochromatosis and thalassemia, iron overload can cause heart failure, liver cancer, liver cirrhosis, arthropathy, and endocrine problems. In sickle-cell disease, iron overload contributes to increased mortality, organ failure, and liver cirrhosis, among other health effects. Detecting iron overload is important not only because of its prevalence and health effects, but because there exist effective therapies, such as chelators and other treatment regimens such as phlebotomy, for these health effects.

The traditional gold standard for assessing body iron stores in the liver is the liver iron concentration ("LIC"), as determined by biochemical analysis of a biopsy specimen. However, liver biopsy is highly invasive and painful, and carries a small but definite risk of severe bleeding. Because of biopsy's invasiveness, many clinicians rely on indirect iron measurements such as serum ferritin. However, serum ferritin is unreliable because it is affected by other factors such as inflammation, liver disease, infection, hemolysis, and other health effects.

Magnetic Resonance Imaging ("MRI") is a technique for indirectly measuring liver iron levels non-invasively, through its effect on spin relaxation times of nearby water molecules. However, MRI liver iron measurements performed at a single field strength remain uncertain due to the complexity of the spin-relaxation mechanism, and its dependence on tissue properties other than the iron concentration itself. MRI measurements at two (or more) field strengths can help resolve this uncertainty since the spin-spin relaxation rate is weakly dependent on the applied static field, while the relaxation due to the presence of iron is strongly dependent on the static magnetic field. By varying the static field, it is possible to determine how much of the relaxation is due to the presence of iron and how much is due to spin-spin coupling. Currently, in order to make the two-field MRI measurements, one has to perform a measurement at one static field, remove the sample from the MRI unit, and place the sample into another MRI unit of different field strength. Since MRI units are expensive, many smaller hospitals and MRI centers may not have multiple MRI units and will not be able to perform the multiple-field measurements. Moreover whole-body MRI has disadvantages in cost and accessibility. An abdominal MRI scan cost at least $600 (in 2006 dollars), and scheduling the scan and waiting for the results of a single MRI can take days or weeks, with the costs and delays likely increased for two MRI scans. Additionally, current MRI machines are not easily portable.

It is however possible to simplify the magnetic resonance measurement if instead of acquiring images with a MRI machine, one aims to determine the liver iron concentration using just relaxation time measurements (i.e. MR relaxometry). Using an electromagnet whose field strength can be varied by controlling the current in the electromagnet, measurements of the spin relaxation time can be taken at two (or more) magnetic field strengths allowing for an accurate determination of liver iron concentration. However, electromagnets require a power supply and tend to be bulky compared to permanent magnets.

The Los Alamos National Laboratory developed a variable-field permanent magnet dipole ("VFPMD"), which is a c-shaped sector magnet with iron poles separated by a large block of magnet material (SmCo). Moving an iron shunt closer or further away from the back of the magnet, i.e., within a shunt gap formed in a base of the large block of magnet material, can continuously vary the central magnetic field from 0.07 T to 0.3 T. The iron shunt is specially shaped to make the dependence of the dipole field strength on the position of the iron shunt as linear as possible. The dipole has a 2.8 cm high by 8 cm wide aperture with poles that are about 10 cm long. There are several disadvantages associated with the VFPMD, however. First, it is unsuitable for use in clinical diagnostic systems. Rather, it is uniquely designed to meet the particular requirements of the Los Alamos Advanced Free-Electron Laser ("AFEL") experiment, which requires many beam optics and diagnostic elements to be located in a limited area. Second, the configuration of the VFPMD and its method of operation produce significant external field strength, which is undesirable in clinical diagnostic applications because, due to the small size and application of the VFPMD, stray magnetic fields were not a concern. The external field strength produced by the VFPMD, however, is undesirable in clinical diagnostic applications.

A magnetic field adjusting apparatus and a magnetic field adjusting method are disclosed in U.S. Pat. No. 6,448,772 (the "772 patent"). The magnetic field adjusting apparatus disclosed therein is rather complex and uses linear programming to determine where a worker should dispose, as a second and final adjustment to magnetic field uniformity, a number of magnetic field adjusting pieces on a magnetic field generator. The number and location and number of the adjusting pieces that need to be moved are displayed on a display device. Disadvantageously, the method disclosed by the '772 patent relies on manually adding or subtracting small pieces of permanent magnet material. Consequently, adjustments to the magnetic field strength occur in discrete increments, or steps.

What are needed are a low-cost, compact, portable apparatus and methods for performing magnetic resonance imaging with accurate, variable, control of the magnetic field strength during a magnetic resonance measurement, while keeping a relatively uniform magnetic field distribution.

BRIEF DESCRIPTION

Embodiments of an apparatus and methods for varying magnetic field strength in a magnetic resonance system while keeping a relatively uniform magnetic field distribution are disclosed. In an embodiment, a two-pole, generally u-shaped magnet assembly generates a static and uniform magnetic field. The magnet assembly includes two facing magnet poles separated by an air gap. Holes may be formed with the magnet poles. The field control rods may be placed at a pre-determined distance into these holes and symmetrically or asymmetrically moved across each magnet poles in a controlled manner to change the magnetic field strength while keeping the uniform magnetic field distribution. Maximum magnetic field strength may occur when the rods are removed. Minimum magnetic field strength may occur when the rods are fully inserted.

An embodiment of the above-described magnet assembly may be portable, e.g., capable of being wheeled from one location to another. Exemplary applications of embodiments of the magnet assembly described above include, but are not limited to clinical diagnosis (e.g., measuring liver iron levels) and material testing (e.g., inspecting objects (such as bottles) during a screening protocol by measuring a magnetic resonance parameter as a function of the resonance frequency). Other applications are possible and envisioned.

In one aspect, an assembly is provided that includes two facing magnet poles separated by an air gap and configured to generate a static magnetic field having a uniform magnetic field distribution. The assembly also includes two magnetic field adjusting members, each configured to be moved across each magnet pole in a controlled manner to change a strength of the static magnetic field while keeping a uniform magnetic field distribution.

Other features and advantages of the disclosure will become apparent by reference to the following description taken in connection with the accompanying drawings.

BRIEF DESCRIPTION OF THE DRAWINGS

For a more complete understanding of the apparatus and methods for varying field strength in a magnetic resonance system while keeping a relatively uniform magnetic field distribution, and the advantages thereof, reference is now made to the following descriptions taken in conjunction with the accompanying drawings, in which.

DETAILED DESCRIPTION

Figure 1:
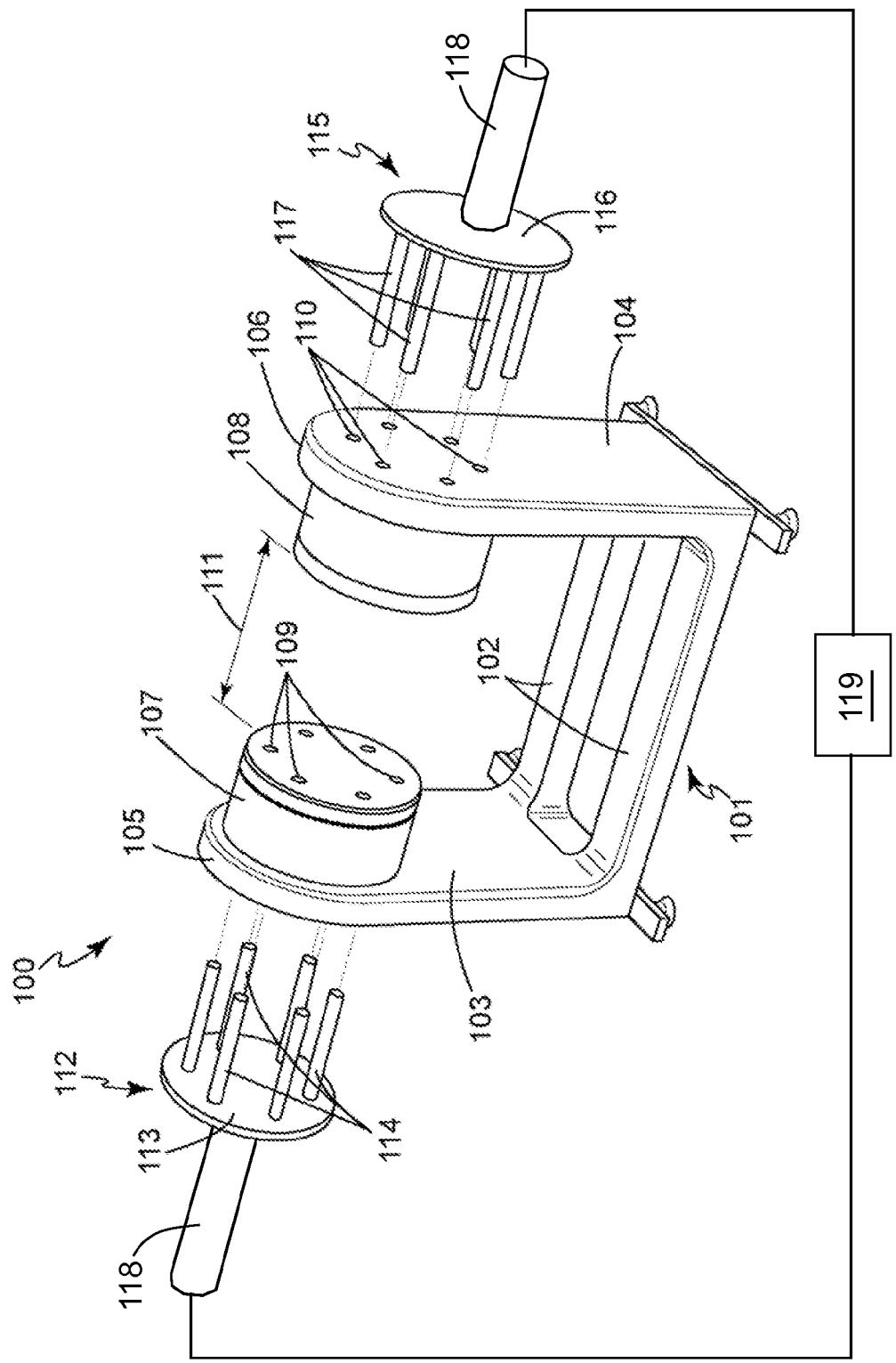
FIG. 1 is a three-dimensional perspective view of an embodiment of a magnet assembly of a nuclear magnetic resonance imaging device.

Magnetic resonance is a technique of radio-frequency (RF) spectroscopy, where the specimen is exposed to a static magnetic field. This field generates a net magnetization (the vector sum of individual nuclear moments) that causes the relevant nuclei in the specimen (e.g., photons from hydrogen, in the case of a human body) to precess about the static magnetic field. The frequency of the precession depends on the applied static magnetic field and the gyro-magnetic ratio of the nucleus, and is known as the Larmour frequency. An externally applied pulse of RF magnetic field at the Larmour frequency causes the net magnetization to tip away from its equilibrium position to a plane that is transverse to the applied static field. Once the RF pulse is removed, the net magnetization begins to slowly (relatively speaking) return to its equilibrium position about the static magnetic field, and in doing so, releases stored up energy in the form of a signal called free induction decay ("FID"). The FID is detected by an RF coil and converted to mathematical data. Depending on the type of clinical diagnosis being performed, repeated magnetic resonance measurements, at various magnetic field strengths may be performed. The mathematical data resulting from the repeated magnetic resonance measurements may be processed (using known data processing techniques) to produce (image or non-image) outputs indicative of a medical condition (e.g., tissue iron levels, etc.).

Once the RF pulse is removed, the net magnetization returns to its equilibrium position about the static magnetic field in a time characterized by the spin-lattice relaxation rate T1. However the FID (representing the transverse magnetization) usually decays faster (characterized by the time T2). As further explained below, this decay is often dominated by magnetic field inhomogeneities and is characterized by T2*. In order to determine T2 (e.g., the FID) a spin echo sequence that cancels the effects of the field inhomogeneities such as the Carr Purcell Meiboom Gill (CPMG) sequence may be used.

Iron in human or animal tissue is predominantly stored as aggregates of ferritin or its breakdown product, hemosiderin. In the strong main magnetic field of an MRI machine, these deposits act to locally augment the magnetic field. These regional disruptions in the magnetic field homogeneity cause precessing water protons to desynchronize with one another, causing the transverse magnetization to decay. Two mechanisms can cause the transverse magnetization to decay. First there is a decay caused by an exchange of energy between the precessing protons and the neighboring atoms. This decay is characterized by the transverse relaxation time T2 or its reciprocal, the transverse relaxation rate R2. The second mechanism for the decay of the transverse relaxation is magnetic field inhomogeneities in the sample that cause the precession rate of the individual protons to vary. The magnetic field inhomogeneities are caused by either the non-uniformity in the applied magnetic field or by the presence of magnetic material (such as iron) in the sample. This field variation de-phases the precessing protons and with time reduces the net transverse magnetization to zero. This characteristic time for the combined effect of the R2 relaxation and that due to magnetic field nonuniformities is the relaxation time T2* (with the corresponding relaxation rate R2*). Additionally, as skilled artisan will appreciate, the spin-spin relaxation rate is weakly dependent on the applied static field, while the relaxation due to the presence of iron is strongly dependent on the static magnetic field. By varying the static field, it is possible to determine how much of the relaxation is due to the presence of iron and how much is due to spin-spin coupling.

In an embodiment, the proposed liver iron measurement the measurement of the MR relaxation times together with the multi-field capability provides a combination of lower cost and potential to obtain a more accurate measure of liver iron at the expense of not getting an MRI image.

Magnet Yoke and Portability:

FIG. 1 is a three-dimensional perspective view of an embodiment of a magnet assembly 100 of a nuclear magnetic resonance imaging device (not shown). The magnet assembly 100 includes a u-shaped yoke 101. A first end of a base 102 of the yoke 101 is substantially orthogonally attached to a first flange 103 coupled with a magnet pole 107, and a second opposite end of base 102 of the yoke 101 is substantially orthogonally attached to a second flange 104 coupled with a magnet pole 108. The free end 105 of the first flange 103 and the free end 106 of the second flange 104 may each be radiused (e.g., curved).

The yoke 101 is configured to position the magnet poles 107, 108 to allow a subject to stand or sit with the abdominal area (or other tissue area to be diagnosed) between the pole faces. Wheels can be coupled with the yoke 101 so the magnet assembly 100 can be easily moved either do patient measurement at a different location or for storage. The yoke 101 may be built using ferromagnetic materials like iron and steel.

Magnet Poles:

In one embodiment, a magnet assembly 100 may include two facing magnet poles separated by an air gap and configured to generate a static magnetic field having a uniform magnetic field distribution.

For example, a first magnet pole 107 may be attached to an interior surface of the first flange 103, near the first flange's free end 105. A second magnet pole 108 may be attached to an interior surface of the second flange 104, near the second flange's free end 106 such that the center axes of each magnet pole 107, 108 are substantially aligned. Each magnetic pole 107,108 may comprise a permanent magnet. Any suitable type and size of permanent magnet may be used. However, in one embodiment, each magnet pole 107, 108 may comprise a Neodymium Iron Boron (NdFeB) permanent magnet about ten inches in diameter. In such an embodiment, a gap 111 of about twelve inches between the faces of the magnet poles 107,108 would generate a magnetic field strength of about 0.3 T at about the center of the gap 111. The weight of the magnet unit is estimated to be about 250 kg or less, and the base 102 of the yoke 101 may rest on wheels that make it movable.

The magnet poles 107, 108 may be made out of NdFeB, which has one of the highest saturation magnetic field densities among all the magnetic materials and consequently will provide the highest field for a given volume of material. In order to minimize magnetic field drift due to variations in the ambient temperature, it may be necessary to maintain the pole faces at a constant temperature. This can be easily achieved by wrapping heating tape around the pole faces and automatically controlling the current applied to the tape by measuring a temperature sensor using a simple feedback circuit. The magnet can be maintained at a few degrees Celsius above the ambient room temperature.

Additionally one or more holes 109 may be formed through the first flange 103 and the magnet pole 107 attached thereto. One or more similar holes 110 may be formed through the second flange 104 and the magnet pole 108 attached thereto. The holes 109,110 may be geometrically arranged and circular-shaped as illustratively shown in FIG. 1. In other embodiments, however, the geometrical arrangements and cross-sectional shapes of the holes 108, 100 in FIG. 1 may be modified. Distributing the holes 109,110 in a predetermined manner in each magnet pole 107, 108 allows for a more efficient reduction in the field strength and controls the field distribution. One or more of the holes 109,110 maybe lined with a friction-reducing material, such as but not limited to, Teflon.

Air Gap:

The magnet poles 107, 108 are separated by an air gap 111. The width of the gap 111 (like the overall dimensions and geometry of the magnet assembly 100) will vary depending on the type of nuclear magnetic resonance machine in to which is it incorporated and/or on the type of clinical diagnosis to be performed. For clinical diagnosis, the air gap may be about twelve inches or greater.

Magnetic Field Adjusting Members:

An embodiment of the magnet assembly 100 may further include at least one, and preferably two, magnetic field adjusting members 112, 115. The magnetic field adjusting member 112 may include a substrate 113 (having a circular or other suitable geometry) to which are attached one or more field control rods 114, which maybe either solid or hollow. Similarly, the magnetic field adjusting member 115 may include a substrate 116 to which are attached one or more field control rods 117, which maybe either solid or hollow. The cross-sectional shapes of the field control rods 114,117 matches the cross-sectional shapes of the holes 109, 110, respectively. In addition to, or alternative to, inclusion of a friction-reducing coating applied to the holes 109,110, one or more of the field control rods 114, 117 may be coated with a friction reducing material. The magnetic field adjusting members 112, 115 and the field control rods 114, 117 maybe formed of a ferromagnetic material, such as metal or metal alloy. Iron and steel are examples of a suitable metal.

Each holder 112, 115 may be coupled with a motorized actuator 118. Each motorized actuator 118 may be controlled via a computer 119 coupled thereto and configured to move each holder 112,115 to and between a first fully inserted position and a second fully extracted position. To operate in a magnet with a maximum field of about 0.3 T, each actuator 118 will need to overcome a maximum magnetic force of about 300 N, based on the assumption that the field between the pole faces needs to be dropped to zero from its maximum value by moving the rods 114,117 a predetermined distance inside each magnet pole 107, 108, respectively. This force is well within the ability of relatively compact actuators.

In FIG. 1, the holders 112,115 are illustratively shown in a fully-extracted position, in which the free ends of the field control rods 114,117 are not within the holes 109,110, respectively. In an alternate embodiment, a fully-extracted position may permit the free ends of the field control rods 114, 117 to be proximate or at a predetermined distance within the holes 109, 110, respectively.

In an embodiment, the holders 112, 115 and the field control rods 114, 117 comprise a means for controlling the field strength of the magnet assembly 100, as they are displaced across the magnet poles 107, 108 in a controlled manner. Maximum magnetic field strength may occur when the field control rods 114,117 are fully-extracted. Minimum magnetic field strength may occur when the field control rods 114,117 are fully inserted. Accordingly, the magnetic field strength may increase as at least one of the magnetic field adjusting devices 112, 115 is removed from its corresponding magnet pole 107 or 108, respectively. Similarly, the magnetic field strength may decrease as at least one of the two magnetic field adjusting members 112, 115 is inserted into its corresponding magnet pole 107 or 108, respectively.

On each magnet pole 107, 108, the faces facing the air gap 111 may be covered with solid aluminum plates to ensure that the field control rods 114, 117 do not move out of their respective magnet poles 107, 108.

The two-pole configuration shown in FIG. 1 generates a relatively uniform static magnetic field between the magnet poles 107,108.

RF Coil:

Although not shown, a (single-sided) RF coil may be placed below the two magnet poles 107, 108 and the base 102 of the yoke 101. The RF coil may be coupled with a power source and configured to produce RF signals at the Larmour frequency when energized. The RF coil may also be configured to receive RF FID signals from the human tissue being diagnosed when de-energized.

The RF coil may be designed to be positioned on the side of the patient to orient the RF field effectively orthogonal to the static magnetic field. In an embodiment, the RF coil may be configured to be mounted in a manner that will closely match an abdominal contour. Alternatively, the RF coil may be mounted to a flat substrate.

General Operation:

For measurement of iron levels in human or animal tissue, measurement of MR relaxation times together with a multi-field strength capability provides a combination of lower cost and potential to obtain a more accurate measure of liver iron levels, but at the expense of not getting an MRI image.

For a measurement of iron in human or animal tissue, a two-pole magnet assembly 100 requires a gap 111 that fits a person's (or animal's) abdomen between the magnet poles 107,108 and ensures that the region of best uniformity of the magnetic field (e.g., the "sweet spot") corresponds to the region of the tissue (e.g., liver) whose iron concentration is being measured. In one such embodiment, the gap 111 may be about twelve inches and about 100 ppm magnetic field homogeneity in about one cu. inch volume may be centered around the sweet spot at the center of the gap 111. In other applications, such as material testing of objects (e.g., liquid-filled containers), the gap 111 may be any suitable size and may vary depending on the dimensions of the object tested. In such other applications, the magnetic field homogeneity about the sweet spot may also vary.

An embodiment of the magnet assembly 100 is configured to ensure that a required range of magnetic fields is achieved with the "sweet spot" at each different field corresponding to the same region of tissue (e.g., liver) with the subject's abdomen placed between the opposing faces of the magnet poles 107,108. In such an embodiment, the magnet assembly may be further configured so the field control rods 114, 117 can be moved inside the holes 109,110 in the magnet poles 107, 108 despite the strong magnetic field.

In clinical diagnosis use, the magnet assembly 100 may be part of, or may be coupled with, a diagnostic apparatus configured to measure iron concentration levels in a subject. In one aspect, the diagnostic apparatus is a Magnetic Resonance Imaging device. Tissue (e.g., abdomen, head, etc.) of the subject is positioned within the air gap 111 of the magnet assembly 100 and a magnetic resonance measurement is taken. In an embodiment, the magnetic resonance measurement obtained is the time R2 (transverse relaxation rate) discussed above. Thereafter, the field strength of the static, relatively uniform magnetic field is changed by moving the field control rods 114, 117 with an actuator 118, and another magnetic resonance measurement is taken until R2 data at the required number of magnetic fields (of varying strength) is collected. In an embodiment, at least two magnetic resonance measurements at each of two different magnetic field strengths are taken. The collected R2 data may be computer-processed to output the concentration (or range of concentrations) of iron in the tissue.

In materials testing use, the magnet assembly 100 may be part of, or may be coupled with, a diagnostic apparatus configured to detect one or more detection targets in an object. In one embodiment, the object may be a liquid-containing object. Non-limiting examples of a detection target include explosives, illegal drugs, and/or other materials of interest. The diagnostic apparatus may be a Magnetic Resonance Imaging device. In one aspect, a liquid containing object (not shown) may be positioned with the air gap 111 of the magnet assembly 100 and a magnetic resonance measurement is taken. In an embodiment, the magnetic resonance measurement obtained is the relaxation time as a function of the resonance frequency. Thereafter, the field strength of the static, relatively uniform magnetic field is changed by moving the field control rods 114, 117 with an actuator 118, and another magnetic resonance measurement is taken until relaxation time data at the required number of magnetic fields (of varying strength) is collected. In an embodiment, at least two magnetic resonance measurements at each of two different magnetic field strengths are taken. The collected relaxation time data may be computer-processed to output the concentration (or range of concentrations) of explosives and/or other materials in the liquid.

Range of Magnetic Fields:

Embodiments of the multi-pole magnet described herein may have a maximum field of about 0.3 T and may be capable of operating at field strengths in the range about 0.05-0.3 T. This range may be obtained by changing the position of field control rods 114,117 in holes designed into magnet poles 107, 108 as shown in FIG. 1. If the position of the field control rods 114,117 is/are changed symmetrically in the two magnetic poles 107, 108, the sweet spot will remain at the center of the gap 111 (corresponding to the same region of the tissue being diagnosed (or material being evaluated)).

Volume of the Tissue to be Measured:

The volume of the tissue that will be measured will depend both on the field homogeneity of the multi-pole magnet and the uniformity of the applied RF field. One embodiment measures about a 1 cu. inch volume of tissue, a size much larger than has been traditionally used for liver biopsies. Thus, it is possible to measure different regions of tissue by (a) moving the human subject with respect to the poles 107, 108 of the magnet and (b) asymmetrically positioning the field control rods 114,117 in the two magnetic poles 107,108. The asymmetric positioning will cause one pole to have a stronger field than the other and will consequently move the low field gradient region (the sweet spot) towards the weaker pole face and away from the center of the gap 111. Hence a different region of tissue may be measured with the appropriate RF field.

Electronics:

In an embodiment, the magnet assembly 100 may include and/or be coupled with other digital and/or electronic devices, examples of which include a spectrometer, an RF amplifier, an RF receiver, a computer, and/or a display device.

Figure 2:
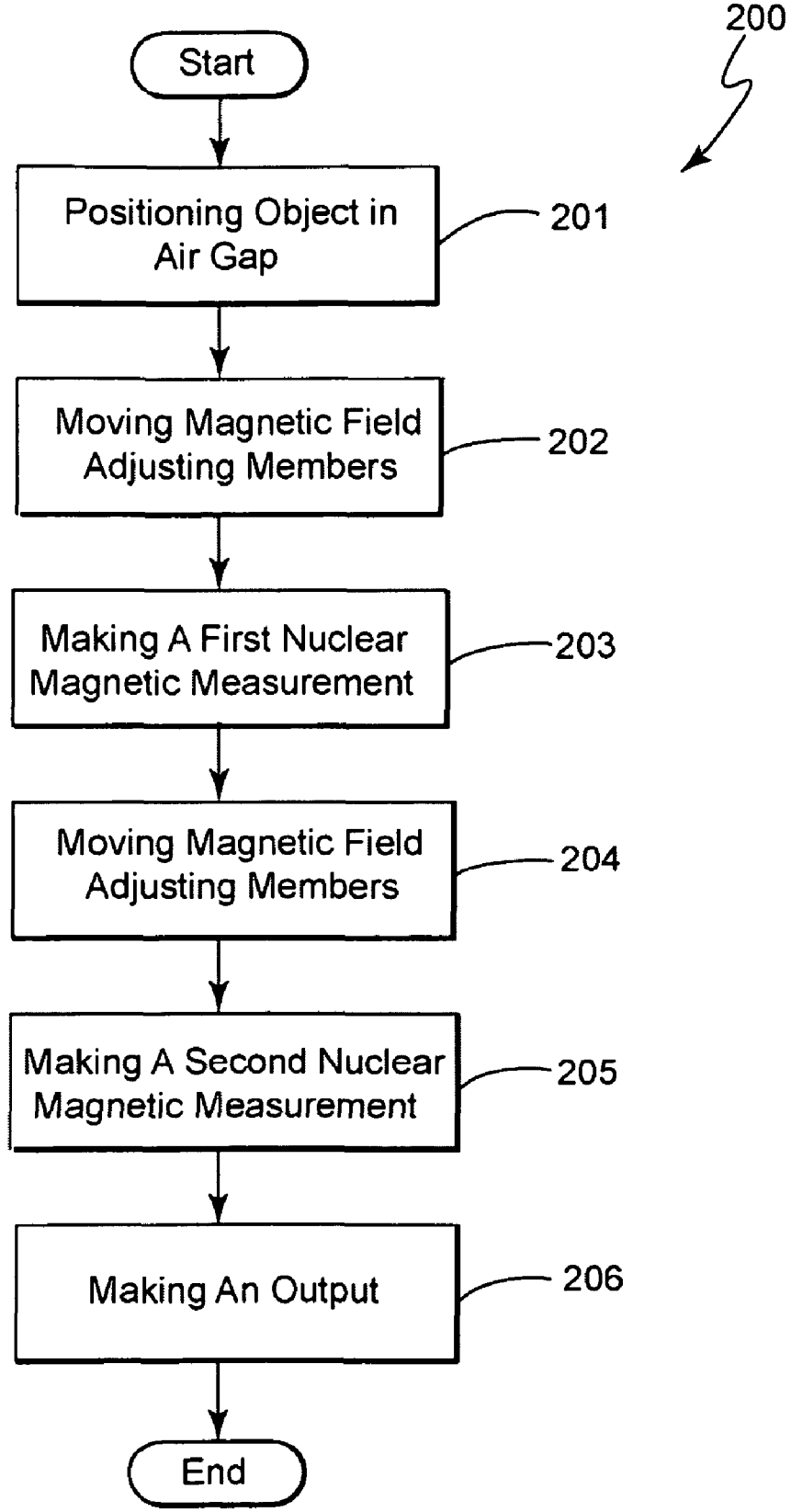
FIG. 2 is a flowchart of a method of operating a magnet assembly.

Methods:

FIG. 2 is a flowchart illustrating an embodiments of a method of operating the magnet assembly 100 of FIG. 1.

Referring to FIGS. 1 and 2, in one embodiment, a method 200 may include the following steps, which may be performed in any suitable order. At a first step 201, an object to be evaluated is positioned in an air gap between a multi-pole magnet, wherein the multi-pole magnet comprises a first magnet pole 107 and second magnet pole 108. At a second step 202, one or more field control rods 114, 115, or magnetic field adjusting members 112, 115, are moved, symmetrically or asymmetrically, to a predetermined position in each of the first and second magnet poles 107, 108 to achieve a predetermined magnetic field strength. At a third step 203, a nuclear magnetic resonance measurement is made. At a fourth step 204, the one or more field control rods 114, or the one or more magnetic field adjusting members 112, 115, are moved to a second predetermined position in each of the first and second magnet poles 107,108 to achieve a second predetermined magnetic field strength. At a fifth step 205, a second nuclear magnetic resonance measurement is made. At a sixth step 206, an output is made based on processing of the first and second nuclear magnetic resonance measurements. In one embodiment, the output may be a concentration (or range of concentrations) of iron levels in tissue. In another embodiment, the output may be a concentration (or range of concentrations) of an explosive, chemical, or other material. In another embodiment, the output may be a probability (or range of probabilities) that an explosive, chemical, or other material exists in the object to be evaluated.

In another embodiment, a method may comprise the following steps. At a first step, a multi-pole magnet assembly 100 may be provided, wherein the magnet poles 107, 108 are separated by an air gap 111. Each magnet pole 107, 108 may include one or more holes 109, 110 therein. At a second step, one or more field control rods 114, 115 may be placed at a pre-determined distance within the holes 109, 110 to change a magnetic field strength while keeping a uniform magnetic field distribution.

The components and arrangements of the apparatus and methods, shown and described herein are illustrative only. Although only a few embodiments of the invention have been described in detail, those skilled in the art who review this disclosure will readily appreciate that substitutions, modifications, changes and omissions may be made in the design, operating conditions and arrangement of the preferred and other exemplary embodiments without departing from the spirit of the embodiments as expressed in the appended claims. The words "including", "comprising", "having", and "with" as used herein are to be interpreted broadly and comprehensively and are not limited to any physical interconnection. Moreover, any embodiments disclosed herein are not to be interpreted as the only possible embodiments. Rather, modifications and other embodiments are intended to be included within the scope of the appended claims.

What is claimed is:

1. An apparatus, comprising:
    a yoke comprising a base, a first flange attached orthogonally to the base and having a first free end, and a second flange attached orthogonally to the base and having a second free end, the second flange spaced apart from the first flange;
    a first magnet pole attached to the first free end and comprising a first permanent magnet;
    a second magnet pole attached to the second free end and comprising a second permanent magnet, the first magnet pole and the second magnet pole defining an air gap therebetween, and the first magnet pole and the second magnet pole configured to generate a static magnetic field having a uniform magnetic field distribution and a static magnetic field strength in the air gap; and
    a first magnetic field adjusting member comprising a first substrate and a first plurality of field control rods coupled to a face of the first substrate.

2. The apparatus of claim 1, wherein the yoke is configured to be movable to different locations.

3. The apparatus of claim 1, wherein the first free end comprises a first plurality of holes formed therethrough, and the second free end comprises a second plurality of holes formed therethrough.

4. The apparatus of claim 3, wherein the first magnet pole comprises a third plurality of holes formed therein that align with the first plurality of holes, and the second magnet pole comprises a fourth plurality of holes formed therein that align with the second plurality of holes.

5. The apparatus of claim 4, wherein the first plurality of field control rods are configured to be moveable through the first plurality of holes and the third plurality of holes, the apparatus further comprising:
    a second magnetic field adjusting member comprising a second substrate and a second plurality of field control rods coupled to a face of the second substrate, the second plurality of field control rods configured to be movable through the second plurality of holes and the fourth plurality of holes,
    the first magnetic field adjusting member configured to be moved across the first magnet pole through the first plurality of holes and the third plurality of holes and the second magnetic field adjusting member configured to be moved across the second magnet pole through the second plurality of holes and the fourth plurality of holes in a controlled manner that changes the static magnetic field strength while the uniform magnetic field distribution stays substantially the same.

6. The system in accordance with claim 5, further comprising:
    a first actuator operatively coupled to the first magnetic field adjusting member configured to control a movement of the first magnetic field adjusting member across the first magnet pole through the first plurality of holes and the third plurality of holes; and
    a second actuator operatively coupled to the second magnet field adjusting member and configured to control a movement of the second magnetic field adjusting member across the second magnet pole through the second plurality of holes and the fourth plurality of holes.

7. The apparatus of claim 1, further comprising a second magnetic field adjusting member comprising a second substrate and a second plurality of field control rods coupled to a face of the second substrate.

8. The apparatus of claim 7, wherein the first magnetic field adjusting member and the second magnetic field adjusting member are configured to be moved symmetrically with respect to the first magnet pole and the second magnet pole.

9. The apparatus of claim 7, wherein the first magnetic field adjusting member and the second magnetic field adjusting member are configured to be moved asymmetrically with respect to the first magnet pole and the second magnet pole.

10. The apparatus of claim 7, wherein the first magnetic field adjusting member is configured to be moved across the first magnet pole and the second magnetic field adjusting member is configured to be moved across the second magnet pole in a controlled manner that changes the static magnetic field strength while the uniform magnetic field distribution stays substantially the same.

11. The apparatus of claim 7, further comprising:
    a first actuator operatively coupled to the first magnetic field adjusting member configured to control a movement of the first magnetic field adjusting member with respect to the first magnet pole; and
    a second actuator operatively coupled to the second magnet field adjusting member and configured to control a movement of the second magnetic field adjusting member with respect to the second magnet pole.

12. The apparatus of claim 7, wherein each of the first magnetic field adjusting member and the second magnetic field adjusting member comprises a ferromagnetic material.

13. The apparatus of claim 7, wherein the static magnetic field strength increases as at least one of the first magnetic field adjusting member is removed from the first magnet pole and the second magnetic field adjusting member is removed from the second magnet pole.

14. The apparatus of claim 7, wherein the static magnetic field strength decreases as at least one of the first magnetic field adjusting member is inserted into the first magnet pole and the second magnetic field adjusting member is inserted into the second magnet pole.

15. A system, comprising:
a diagnostic apparatus; and
a magnet assembly coupled to the diagnostic apparatus, the magnet assembly comprising:
- a yoke comprising a base, a first flange attached orthogonally to the base and having a first free end, and a second flange attached orthogonally to the base and having a second free end, the second flange spaced apart from the first flange;
- a first magnet pole attached to the first free end and comprising a first permanent magnet;
- a second magnet pole attached to the second free end and comprising a second permanent magnet, the first magnet pole and the second magnet pole defining an air gap therebetween, and the first magnet pole and the second magnet pole configured to generate a static magnetic field having a uniform magnetic field distribution and a static magnetic field strength within the air gap; and
- a first magnetic field adjusting member comprising a first substrate and a first plurality of field control rods coupled to a face of the first substrate.

16. The system of claim 15, wherein the diagnostic apparatus is configured to detect one or more detection targets.

17. The system of claim 15, wherein the diagnostic apparatus is a magnetic resonance imaging device.

18. The system of claim 15, further comprising a second magnetic field adjusting member comprising a second substrate and a second plurality of field control rods coupled to a face of the second substrate.

19. The system of claim 18, wherein the first magnetic field adjusting member is configured to be moved across the first magnet pole and the second magnetic field adjusting member is configured to be moved across the second magnet pole in a controlled manner that changes the static magnetic field strength while the uniform magnetic field distribution stays substantially the same.

20. The system of claim 18, wherein the diagnostic apparatus is configured to:
- take a first magnetic resonance (MR) measurement with the first magnetic field adjusting member and the second magnetic field adjusting member at first positions with respect to the first magnet pole and the second magnet pole;
- take a second MR measurement with the first magnetic field adjusting member and the second magnetic field adjusting member at second positions with respect to the first magnet pole and the second magnet pole, the second positions different than the first positions; and
- determine iron concentration levels using the first MR measurement and the second MR measurement.

* * * * *